US009943869B2

(12) United States Patent
Huang et al.

(10) Patent No.: US 9,943,869 B2
(45) Date of Patent: Apr. 17, 2018

(54) SELF-POWERED SHOWERHEAD

(71) Applicants: Chun-Ming Huang, Hsinchu (TW); Chen-Chia Chen, Hsinchu (TW); Chien-Ming Wu, Hsinchu (TW)

(72) Inventors: Chun-Ming Huang, Hsinchu (TW); Chen-Chia Chen, Hsinchu (TW); Chien-Ming Wu, Hsinchu (TW)

(73) Assignee: NATIONAL APPLIED RESEARCH LABORATORIES, Hsinchu (TW)

( * ) Notice: Subject to any disclaimer, the term of this patent is extended or adjusted under 35 U.S.C. 154(b) by 0 days.

(21) Appl. No.: 15/161,278

(22) Filed: May 22, 2016

(65) Prior Publication Data

US 2017/0252764 A1 Sep. 7, 2017

Related U.S. Application Data

(63) Continuation-in-part of application No. 15/059,356, filed on Mar. 3, 2016.

(30) Foreign Application Priority Data

Apr. 12, 2016 (TW) .............................. 105205037 A

(51) Int. Cl.
| | |
|---|---|
| *B05B 12/08* | (2006.01) |
| *B05B 1/18* | (2006.01) |
| *G01N 25/00* | (2006.01) |
| *G01F 1/00* | (2006.01) |
| *H02P 9/02* | (2006.01) |
| *E03C 1/04* | (2006.01) |
| *B05B 12/00* | (2018.01) |

(52) U.S. Cl.
CPC .............. *B05B 12/008* (2013.01); *B05B 1/18* (2013.01); *G01F 1/00* (2013.01); *G01N 25/00* (2013.01); *H02P 9/02* (2013.01); *E03C 2001/0418* (2013.01)

(58) Field of Classification Search
CPC ....... B05B 1/18; B05B 12/004; B05B 12/008; E03C 2001/0418; E03C 1/0404; F03B 13/00; F05B 2220/602; H02K 7/1823; Y02B 10/50; G01F 1/00; G01N 25/00; H02P 9/02
USPC ....... 239/71–74, 552, 556–561, 567; 290/43, 290/54; 362/96, 192
See application file for complete search history.

(56) References Cited

U.S. PATENT DOCUMENTS

| | | | | |
|---|---|---|---|---|
| 4,936,508 A | * | 6/1990 | Ingalz ..................... | G01F 1/115 137/551 |
| 7,252,431 B1 | * | 8/2007 | Caramanna .............. | G01K 1/14 116/216 |
| 8,448,664 B2 | * | 5/2013 | Lin .......................... | E03B 7/07 137/119.05 |
| 2004/0258567 A1 | * | 12/2004 | Kokin ................... | E03C 1/0404 422/68.1 |
| 2005/0004712 A1 | | 1/2005 | Stevens et al. | |

(Continued)

*Primary Examiner* — Arthur O Hall
*Assistant Examiner* — Cody Lieuwen

(57) ABSTRACT

The showerhead includes a main body; a power generator disposed in the main body; a power monitor module, disposed in the main body, electrically connected to the power generator, and configured for monitoring quality of power from the power generator and switching on/off power supply of the power generator; and a control module, disposed in the main body, electrically connected to the power monitor module, and configured for controlling functions.

15 Claims, 4 Drawing Sheets

(56) References Cited

U.S. PATENT DOCUMENTS

| | | | |
|---|---|---|---|
| 2006/0045167 A1* | 3/2006 | Pawlenko | G01K 1/028 |
| | | | 374/148 |
| 2009/0121044 A1* | 5/2009 | Lo | E03C 1/0404 |
| | | | 239/71 |
| 2011/0071698 A1* | 3/2011 | Glasser | F03B 13/00 |
| | | | 700/296 |
| 2012/0090561 A1 | 4/2012 | Chen | |
| 2013/0333764 A1* | 12/2013 | Wright | E03C 1/02 |
| | | | 137/1 |

* cited by examiner

SELF-POWERED SHOWERHEAD

CROSS-REFERENCE TO RELATED APPLICATIONS

This application is a continuation-in-part of U.S. patent application Ser. No. 15/059,356, filed Mar. 3, 2016, now pending.

BACKGROUND OF THE INVENTION

1. Technical Field

The invention relates to showerheads, particularly to electrically controlled showerheads.

2. Related Art

Showering is common in Western culture due to the efficiency of using it compared to a bathtub. Its use in hygiene is therefore common practice. A shower uses less water on average than a bath: 80 liters for a shower compared to 150 liters for a bath. The simplest showers have a swiveling nozzle aiming down on the user, while more complex showers have a showerhead connected to a hose that has a mounting bracket. This allows the showered to spray the water at different parts of their body.

With the progress of technology, showerheads can perform additional functions other than spraying water. For example, a showerhead provided with a temperature display area which is made of a temperature-sensitive material for showing water temperature by color. Furthermore, some showerheads are provided with a digital display or a function of adjusting water temperature.

However, such a multifunctional showerhead needs supply of electricity. A common solution is to dispose a battery to supply electricity. The battery in a showerhead tends to be moisturized and needs to be replaced repeatedly. This is inconvenient for users. There is no solution in the market yet.

SUMMARY OF THE INVENTION

An object of the invention is to provide a self-powered showerhead, which can generate electricity by water flow to supply an electronic device in the showerhead.

To accomplish the above object, the self-powered showerhead of the invention includes a main body; a power generator disposed in the main body; a power monitor module, disposed in the main body, electrically connected to the power generator, and configured for monitoring quality of power from the power generator and switching on/off power supply of the power generator; and a control module, disposed in the main body, electrically connected to the power monitor module, and configured for controlling functions.

DETAILED DESCRIPTION OF THE INVENTION

Figure 1:
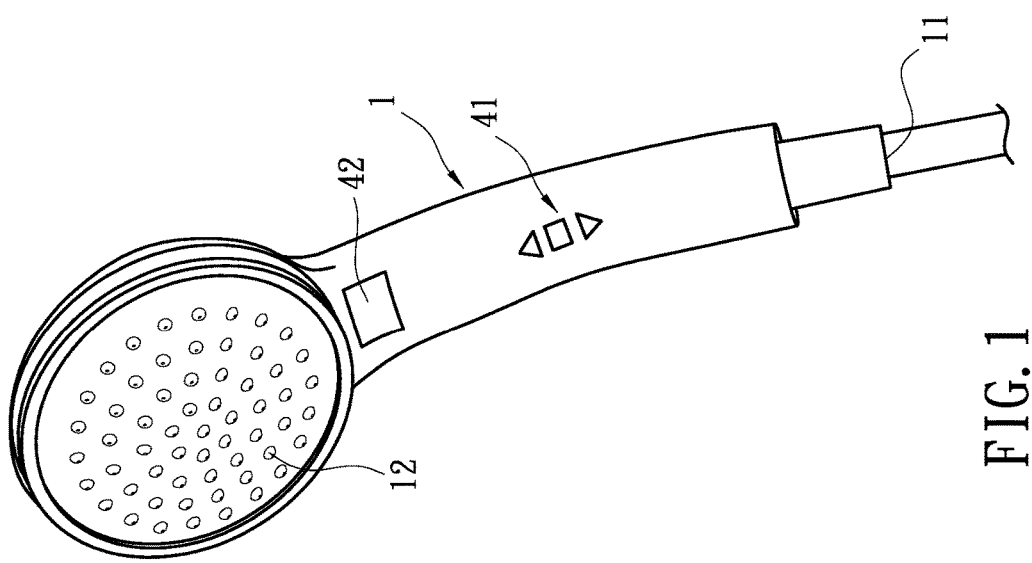
FIG. 1 is a perspective view of the invention.
Figure 2:
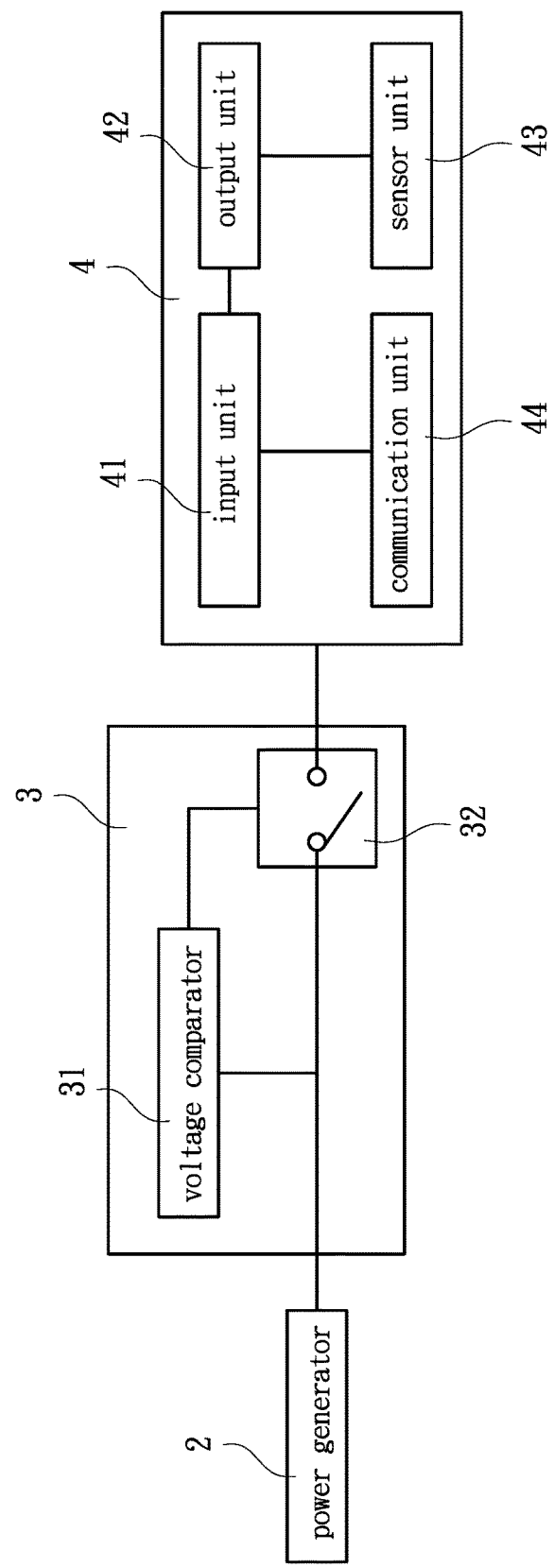
FIG. 2 is a block diagram of the first embodiment of the invention.

Please refer to FIGS. 1 and 2. The self-powered showerhead of the invention includes a main body 1. The main body 1 is hollow and has an inlet 11 and a nozzle 12. A power generator 2, a power monitor module 3 and a control module 4 are disposed in the main body 1. The power generator 2 communicates with the inlet 11 so that the water flow from the inlet 11 can drive the power generator 2 to generate electric power.

Please refer to FIG. 2. The power generator 2 is electrically connected to the power monitor module 3. The power monitor module 3 is used for monitoring the quality of output electricity from the power generator 2 to guarantee the voltage of the power generator 2 is sufficient. Also, the power monitor module 3 can switch on or off the electricity supply of the power generator 2 depending upon the voltage of the power generator 2. In this embodiment, the power monitor module 3 includes a voltage comparator 31 and a switch 32. The voltage comparator 31 is electrically connected to the switch 32. The power monitor module 3 receives the voltage of the electricity supply of the power generator 2, and the voltage comparator 31 monitors the voltage. The voltage comparator 31 drives the switch 32 to close the circuit when the voltage is greater than a threshold so that the electricity from the power generator 2 can be supplied to the control module 4. Contrarily, the voltage comparator 31 drives the switch 32 to open the circuit when the voltage is less than a threshold so as to disconnect the power generator 2 from the control module 4.

The power monitor module 3 is electrically connected to the control module 4. The control module 4 includes an input unit 41, an output unit 42, a sensor unit 43 and a communication unit 44. The input unit 41 is one or more keys mounted on the main body 1 for operation. The output unit 42 is electrically connected to the input unit 41. The output unit 42 may be a display mounted on the main body 1 for showing information. The sensor unit 43 is electrically connected to the output unit 42 for sensing temperature of the water flow or flow rate of the water flow in the main body 1. The temperature or flow rate can be shown on the output unit 42. Finally, the communication unit 44 is electrically connected to the input unit 41 for transmitting wireless signals to an external device (not shown) or receiving wireless signals from an external device (not shown). For example, the communication unit may be a Wi-Fi module or a Bluetooth® module.

Figure 3:
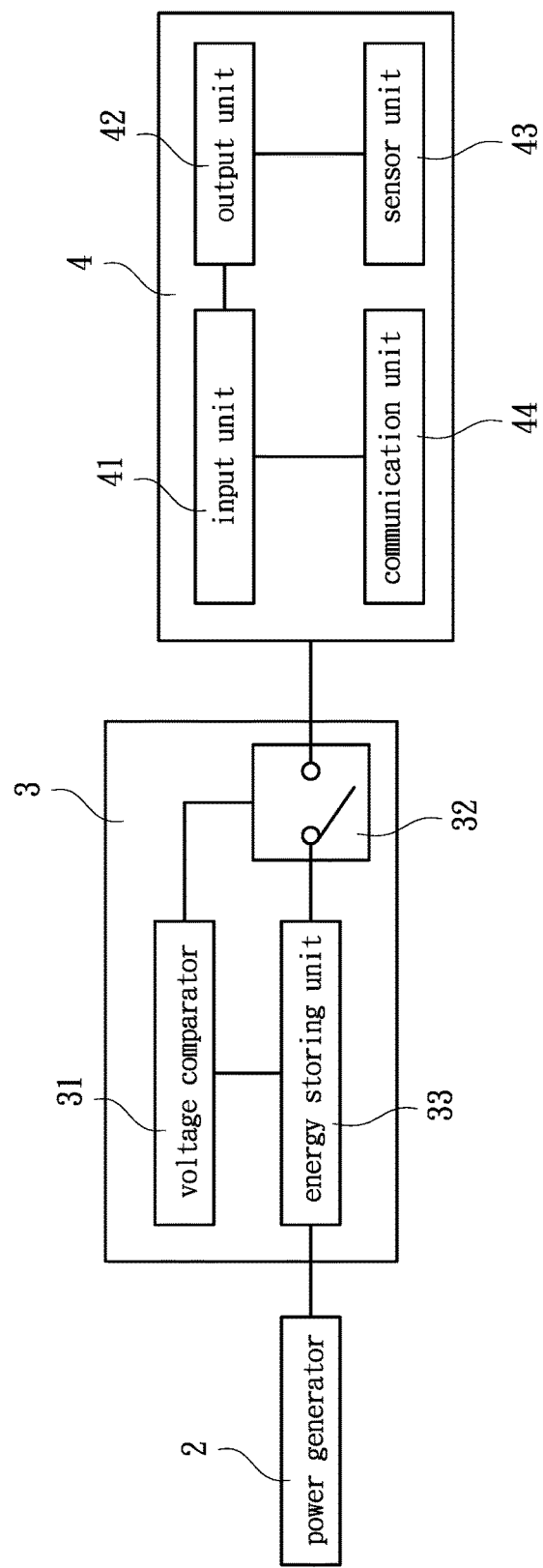
FIG. 3 is a block diagram of the second embodiment of the invention.

Please refer to FIG. 3, which shows a second embodiment of the invention. In this embodiment, the power monitor module 3 includes a voltage comparator 31, a switch 32 and an energy storing unit 33. The energy storing unit 33 may be a capacitor, which is electrically connected between the power generator 2, the voltage comparator 31 and the switch 32. The voltage comparator 31 is electrically connected to the switch 32. When the electricity from the power generator 2 enters the energy storing unit 33 of the power monitor module 3, the voltage comparator 31 monitors the voltage of the energy storing unit 33. The voltage comparator 31 drives the switch 32 to open the circuit when the voltage is less than a threshold so as to charge the energy storing unit 33. Contrarily, the voltage comparator 31 drives the switch 32 to close the circuit when the voltage is greater than a threshold so that the electricity from the power generator 2 can be supplied to the control module 4.

Figure 4:
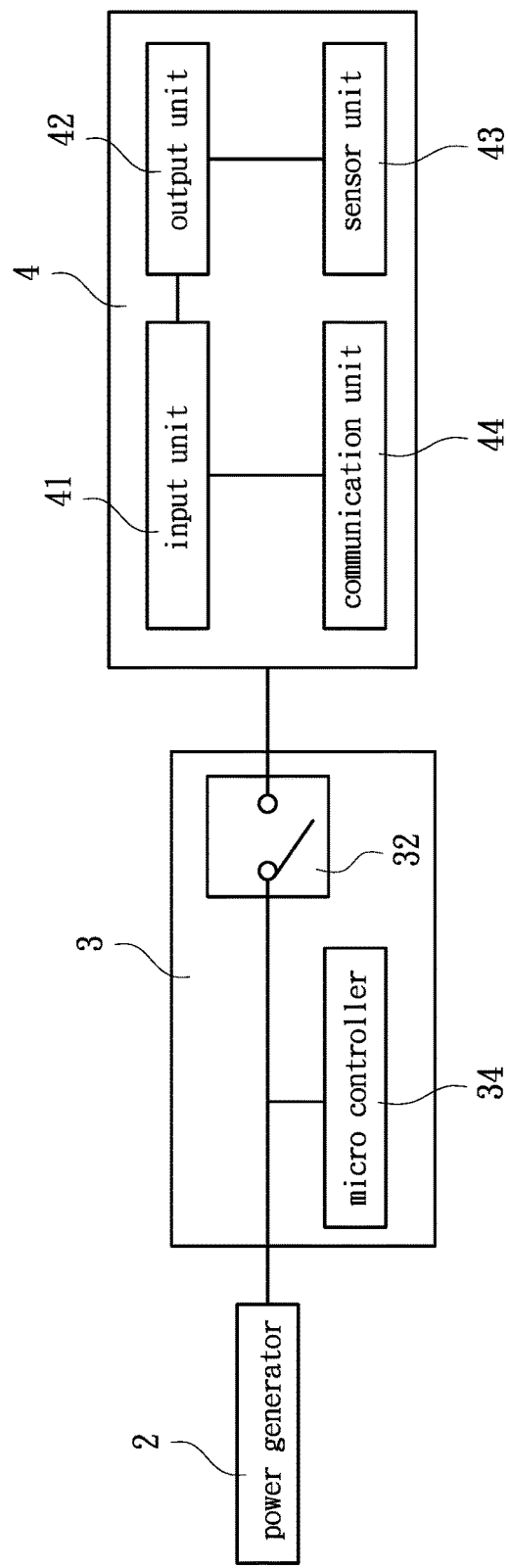
FIG. 4 is a block diagram of the third embodiment of the invention.

Please refer to FIG. 4, which shows a third embodiment of the invention. In this embodiment, the power monitor module 3 includes a micro controller 34 and a switch 32. The micro controller 34 is electrically connected between the power generator 2 and the switch 32. The micro controller 34 drives the switch 32 to close the circuit when the voltage of the power generator 2 is greater than a threshold so that the electricity from the power generator 2 can be supplied to the control module 4.

It will be appreciated by persons skilled in the art that the above embodiments have been described by way of example only and not in any limitative sense, and that various alterations and modifications are possible without departure from the scope of the invention as defined by the appended claims.

What is claimed is:

1. A showerhead comprising:
   a showerhead main body;
   a power generator disposed in the showerhead main body;
   a power monitor module, disposed in the showerhead main body, electrically connected to the power generator, and configured for monitoring voltage of electric power from the power generator and switching on/off power supply of the power generator depending on the voltage of the power generator; and
   a control module, disposed in the showerhead main body, electrically connected to the power monitor module, and configured for controlling functions;
   wherein the power monitor module directly switches on or off the electric power from the power generator to the control module, and the electric power from the power generator is directly connected to the control module without a battery when the power monitor module switches on.

2. The showerhead of claim 1, wherein the power generator is a hydroelectricity module.

3. The showerhead of claim 1, wherein the showerhead main body has an inlet and a nozzle.

4. The showerhead of claim 3, wherein the power generator communicates with the inlet.

5. The showerhead of claim 1, wherein the control module further comprises an input unit mounted on the showerhead main body.

6. The showerhead of claim 5, wherein the input unit is at least one key.

7. The showerhead of claim 5, wherein the control module further comprises an output unit which is electrically connected to the input unit and mounted on the showerhead main body for showing information from the control module.

8. The showerhead of claim 7, wherein the output unit is a display mounted on the showerhead main body.

9. The showerhead of claim 7, wherein the control module further comprises a sensor unit electrically connected to the output unit for sensing temperature of water flow and measuring flow rate of water flow in the showerhead main body.

10. The showerhead of claim 5, wherein the control module further comprises a communication unit electrically connected to the input unit for transmitting wireless signals to an external device or receiving wireless signals from an external device.

11. The showerhead of claim 10, wherein the communication unit is a Wi-Fi module.

12. The showerhead of claim 1, wherein the power monitor module further comprises a voltage comparator and a switch, the voltage comparator is electrically connected to the switch for monitoring a voltage of the power generator and driving the switch to open or close.

13. The showerhead of claim 1, wherein the power monitor module further comprises a voltage comparator and energy storing unit, which is electrically connected between the power generator and the voltage comparator.

14. The showerhead of claim 13, wherein the energy storing unit is a capacitor.

15. The showerhead of claim 1, wherein the power monitor module further comprises a micro controller and a switch, the micro controller is electrically connected between the power generator and the switch for driving the switch to close or open depending upon a voltage of the power generator.

* * * * *